United States Patent [19]

Kraus, Jr. et al.

[11] Patent Number: 4,825,688
[45] Date of Patent: May 2, 1989

[54] APPARATUS FOR SENSING OF MASS IN BATHS

[76] Inventors: Robert P. Kraus, Jr.; Peter E. Davison, both of Eastman Kodak, Rochester, N.Y. 14560

[21] Appl. No.: 160,612

[22] Filed: Feb. 26, 1988

Related U.S. Application Data

[63] Continuation-in-part of Ser. No. 68,858, Jul. 2, 1987, abandoned.

[51] Int. Cl.⁴ .......................... G01N 20/00; G01N 9/24
[52] U.S. Cl. ...................................... 73/61 R; 435/291
[58] Field of Search .................... 73/590, 599, 61.1 R, 73/61 R, 32 R; 250/343, 373; 55/178, 270, 277; 435/291; 99/276, 277, 278

[56] References Cited

U.S. PATENT DOCUMENTS

| 3,111,839 | 11/1963 | Evans | 73/61 R |
| 3,719,090 | 3/1973 | Hathaway | 73/61 R |
| 3,737,844 | 6/1973 | Yokoyama et al. | 73/599 |
| 4,384,476 | 5/1983 | Black et al. | 73/61 R |

FOREIGN PATENT DOCUMENTS 0602540 10/1987 U.S.S.R. .............................. 435/291

OTHER PUBLICATIONS

Dell'Ova et al., "Ultrasonic Degasser for Use in Liquid Chromatography" Analytical Chemistry, vol. 46, No. 9, pp. 1365–1366, Aug. 1974.

Primary Examiner—Stewart J. Levy
Assistant Examiner—Lawrence G. Fess

[57] ABSTRACT

There is disclosed an apparatus for use in an aerated bath comprising a sensor to sense mass concentration within a liquid, a debubbler for forcing bubbles from the portion of the liquid to be sensed by the sensor, away from the sensor, and a flow limiter to limit liquid flow past the sensor to no more than that rate at which the debubbler can force bubbles away from the portion to be sensed. The debubbler removes bubbles and the sensor senses mass concentration without removal of liquid from the confines of the bath and before the liquid portion is reaerated by the bath. A process of sensing in the absence of bubbles is also disclosed.

10 Claims, 7 Drawing Sheets (SIDE VIEW)

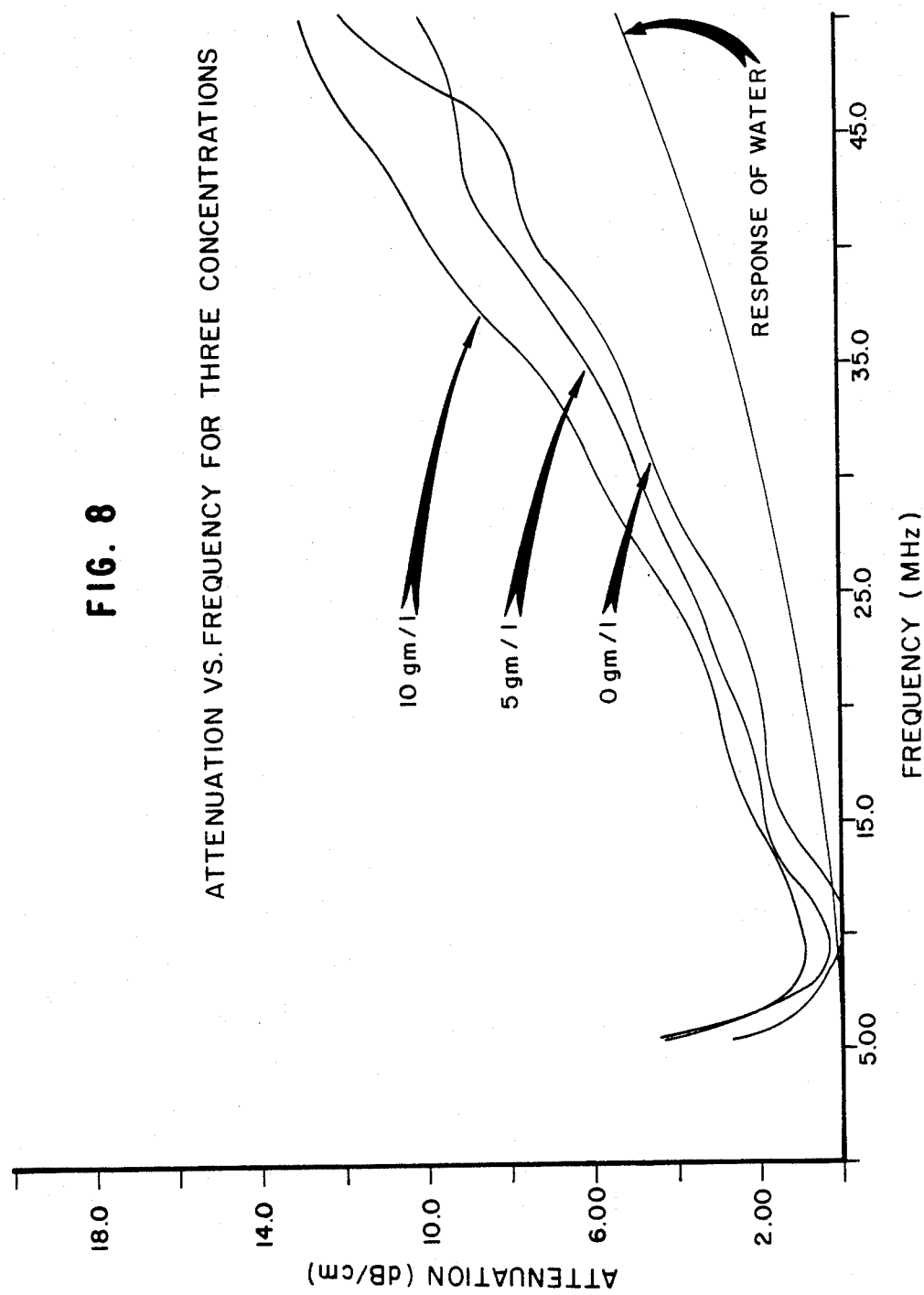

APPARATUS FOR SENSING OF MASS IN BATHS

FIELD OF THE INVENTION

This invention relates to sensing apparatus for determining component concentrations in a bath, such as cell mass in a fermenter, and particularly one that must eliminate bubbles for an effective measurement.

BACKGROUND OF THE INVENTION

Ultrasound is one known method for analyzing microbial populations such as are grown in fermenters. Such a technique is described, for example, in *Applied and Environmental Microbiology*, Vol. 42, p. 632–637 (1981) and in *J. of the Accoustical Society of America*, Vol. 31, pp. 185–189 (1959). The process is based upon the fact that the bulk properties of the dispersion change with cell growth. This is in turn affects the rate of attenuation of the ultrasound waves.

However, this is considerable difficulty in making such measurements within the fermenter itself. A chief difficulty is that the fermentation liquid of necessity is aerated, and the presence of bubbles (from 10 to 15% of the volume) grossly distorts the ultrasound attenuation so as to suggest an apparent change to the overall density. (As used herein, "aerated" refers to the presence of gas bubbles of any suitable composition, such as air in the case of aerobic microbes, and ammonia in the case of anaerobic microbes.) One solution to this would be to remove sample from the fermenter to an off-line location. However, this requires extensive equipment and delay, so that the measurement being taken may not be an accurate measurement of instantaneous conditions as they exist in the fermenter. The opposite solution of measuring within the fermenter has not seemed desirable in the past due to the omnipresent bubbles. That is, if a portion of the fermenter volume is debubbled prior to making the measurement, it is sure to become reaerated almost instantly, so that a bubble-free measurement did not appear to be possible.

Yet another approach has been to attempt to make the ultrasound measurement in a portion of the fermenter that is free of the bubbles. Such an approach is suggested in Japanese Kokai No. 61/74573. The difficulty with this method is that in many cases, the aeration occurs throughout the fermenter, so that no place is completely free of bubbles. It is unrealistic therefore to attempt to identify the portion of the fermenter that is free of bubbles.

On-line sensing of fermentation baths has been described, using a debubbling means, in *Biotechnology and Bioengineering Symp.*, No. 9, page 103–116 (1979). However, debubbling is done by a passive, complex density separation rather than an active debubbling technique. Thus, there is no forcing of the bubbles away from the sensor portion. In addition, the liquid follows a long, tortuous path that encourages deposits to form. Such deposits render cleaning difficult, if not impossible. Finally, because density separation is used for the bubbles, it is not possible to entirely submerge the device (shown in FIG. 7 of the article). Instead, the top portion must project above the liquid to allow the bubbles to communicate with the atmosphere above the liquid. At the same time, however, the liquid inlet of the apparatus must be below the liquid level, so that the apparatus becomes very sensitive to that liquid level.

SUMMARY OF THE INVENTION

This invention solves the aforementioned dilemma by providing apparatus that permits a portion of the liquid to be debubbled while still in the bath, and to remain debubbled for the time of the sensing of the concentration. For example, it has been found that this can be done by isolating a portion of the liquid so that the bath flow rate there-through is no more than 6.5 cc/sec.

More specifically, in accord with one aspect of the invention, there is provided, for use in an aerated bath, apparatus comprising (a) means for sensing mass concentration within the liquid, (b) debubbling means for removing bubbles from the portion of the liquid that is to be sensed by the sensing means, away from the sensing means and (c) means for limiting introduction of liquid into the operative space within said sensing means to no more than the rate at which the debubbling means forces away the bubbles, whereby the debubbling means is effective to remove bubbles and the sensing means is effective to sense mass concentration, without removal of liquid from the confines of the bath and before the liquid portion is reaerated by the bath.

In accord with another aspect of the invention, there is provided apparatus comprising (a) means for sensing mass concentration within the liquid, (b) ultrasonic debubbling means comprising an ultrasonic transducer and means for driving the transducer at a frequency of between about 20 KHz and about 50 MHz, and (c) means for limiting introduction of liquid into the operative space within said sensing means to no more than the rate at which the debubbling means forces away the bubbles;

whereby the debubbling means is effective to remove bubbles and the sensing means is effective to sense cell concentration, without removal of liquid from the confines of the bath and before said liquid portion is reaerated by said bath.

In accord with yet another aspect of the invention, there is provided a process for sensing mass concentration. The process comprises the steps of (a) positioning within the bath, sensing means for sensing mass concentration, and adjacent thereto, debubbling means for forcing bubbles away from the sensing means;

(b) activating the debubbling means to force bubbles in the vicinity of the sensing means, away from the sensing means, (c) while activating the debubbling means, limiting flow of liquid past the sensing means to no more than the rate at which the debubbling means forces away the bubbles, and (d) also while activating the debubbling means, sensing the mass concentration using the sensing means.

Thus, it is an advantageous feature of the invention that a portion of an aerated bath can be sensed instantaneously for mass concentration, using apparatus that is accurate, readily cleanable and is not sensitive to the level of liquid within the bath.

It is a related advantageous feature of the invention that ultrasonic means can be used to sense conditions existing in a constantly aerated bath.

BRIEF DESCRIPTION OF THE DRAWINGS

FIG. 8 is a plot of ultrasound attenuation vs frequency, measured at different concentrations on apparatus constructed in accordance with the invention.

DESCRIPTION OF THE PREFERRED EMBODIMENTS

This invention is described hereinafter primarily in connection with its use in a fermentation bath to determine cell mass concentration as the microorganisms are grown, preferably using an ultrasound sensor. In addition, the invention is useful in any bath that has to be highly aerated, whether or not the aeration is required to produce growth of proteinaceous substances. For example, it is useful in making turbidity measurements, such measurements being useful in waste water treatments. It is also useful with other kinds of mass concentration sensors, such as optical sensors.

As used herein, "mass" refers to non-liquid substances of any kind, including proteinaceous substances and particulates such as inorganic substances, dust and the like.

Figure 1:
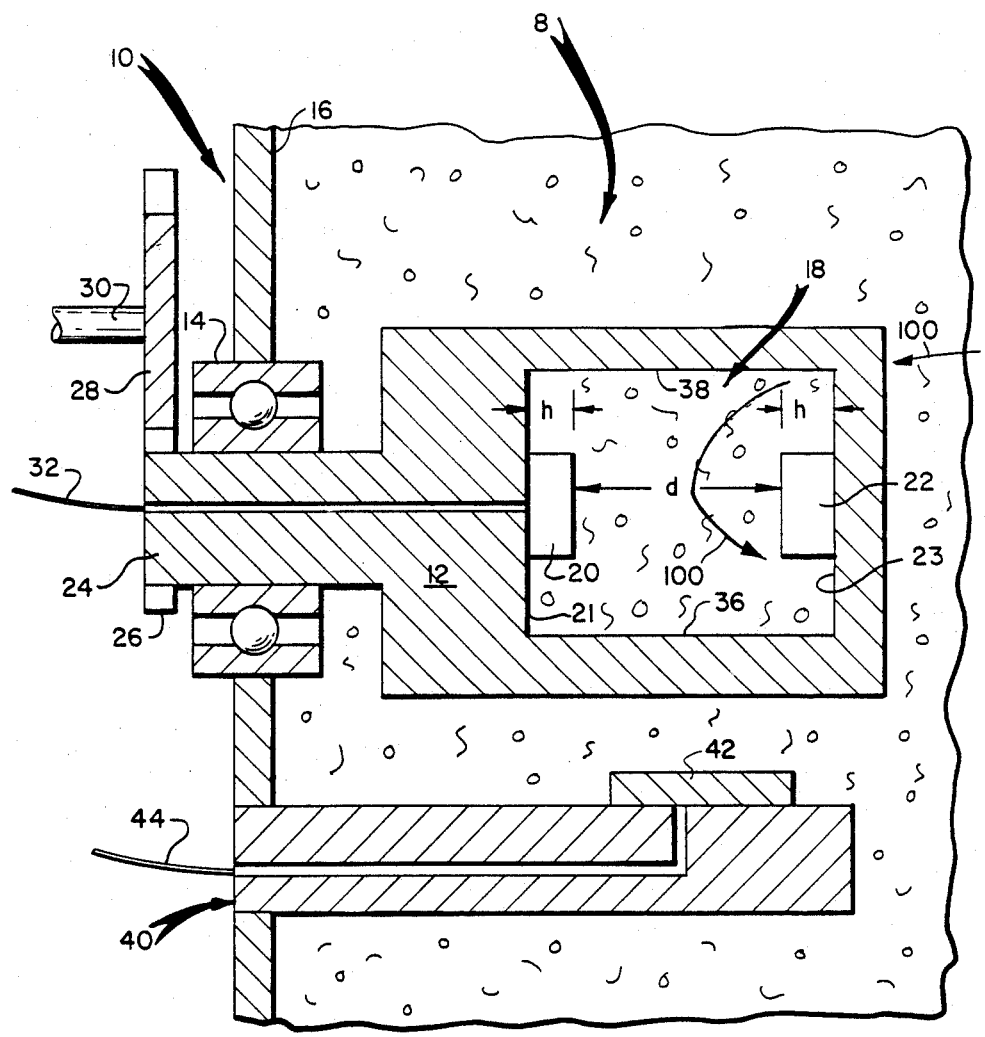
FIG. 1 is a fragmentary elevational view in section through a fermentation bath using the apparatus of the invention.

Thus, as shown in FIG. 1, the apparatus 10 features, in a fermentation bath 8, a frame member 12 mounted for rotation, for example in bearings 14, in wall 16 of the apparatus 10. Member 12 has at one end a cavity 18 containing an ultrasound transducer 20 and a target 22, and at the other end 24, gear means 26 that engages a drive means such as drive gear 28 on a shaft 30 (driven by a suitable motor, not shown.) An electrical line 32 carries power to transducer 20. The transducer is conventional and can comprise any transducer that operates at a frequency of about 10 to 70 MHz. Examples include Panametrics High Frequency Delay Line Series.

Below member 12 is debubbler 40 that is preferably permanently mounted in wall 16.

In accord with one aspect of the invention, cavity 18 is characterized as a free-flow passageway or volume for liquid flow, with the transducer 20 and target 22 held at opposite sides of the passageway by walls 36 and 38. As is apparent from FIG. 1, the passageway is substantially free of constrictions-that is, there are no substantial twists or turns that the liquid has to flow past to traverse the passageway. In addition, the transducer 20 and target 22 project out away from respective surfaces 21 and 23 a distance no greater than h, where h is about 6 mm. Thus, passageway 18 is also free of protrusions having a height greater than about 6 mm, projecting into the path of the liquid from the sidewall surfaces 21, 23 of passageway 18. In the position shown in FIG. 1, passageway 18 is aligned so as to be open to the normal fluid path of bath 8, shown as arrow 100. The bubbles of the bath are shown as circles (whereas the proteinaceous components are not shown.)

Most preferably, the distance "d" between transducer 20 and target 22 is about 8 mm. Optionally, target 22 or transducer 20 can be flush with the surfaces 23 or 21, respectively.

Figure 2:
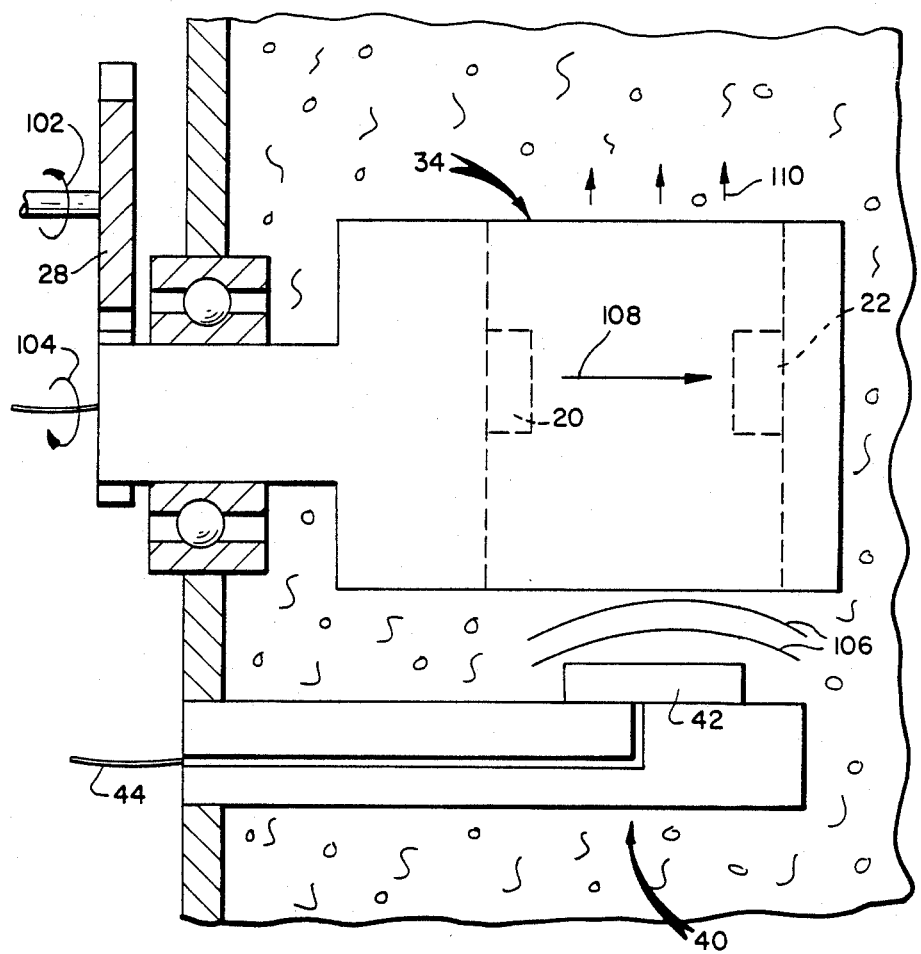
FIG. 2 is a view similar to that of FIG. 1, showing the alternate positioning of the components to achieve debubbling and sensing.

In accord with another aspect of the invention, debubbler 40 features a second ultrasound transducer 42 connected via wires 44 to a power source, and shaped and positioned to emit ultrasonic waves upwardly into and through cavity 18. This of course is not possible in the positions shown in FIG. 1, inasmuch as wall 36 is in the way. Instead, FIG. 2, shaft 30 rotates 90° as shown by arrow 102, to rotate gear 26 90° oppositely as shown by arrow 104, so that passageway 18 extends up and down. At this point, the liquid within passageway 18 becomes temporarily isolated from current 100, so that the constant stream of bubbles normally present cannot enter cavity 18. That is, the flow rate through passageway 18 is reduced to substantially a zero flow rate, discounting eddy currents. The actuation of debubbler 40 causes the emission of ultrasound waves 106, which drives any bubbles within passageway out of cavity or passageway 18, as is well-known, as shown by arrows 110. Thereafter or simultaneously, transducer 20 is activated to create the beam shown by arrow 108. Such beam receives substantially no component of the energy from waves 106, because the two beams are oriented at approximate right angles and the operating frequencies are significantly different.

A variety of ultrasonic devices can be used in the debubbler, as well as in the sensor itself. Useful examples of the debubbler are shown in U.S. Pat. No. 3,904,392 issued on 9/9/75. The preferred frequency of operation is in the range of 20 KHz to higher frequencies, such as 5 MHz. For example, the Vernitron PZT piezoelectric ceramic transducer can be used.

Most preferably, measurement of the attenuation occurring in passageway 18 is done by using a percentage of the first echo off target 22 to create a second wave off transducer 20 that echoes off target 22 thereafter. The transducer thus delivers via line 32 two signals—the first echo and the echo caused by the partial retransmission of the first echo.

Figure 3:
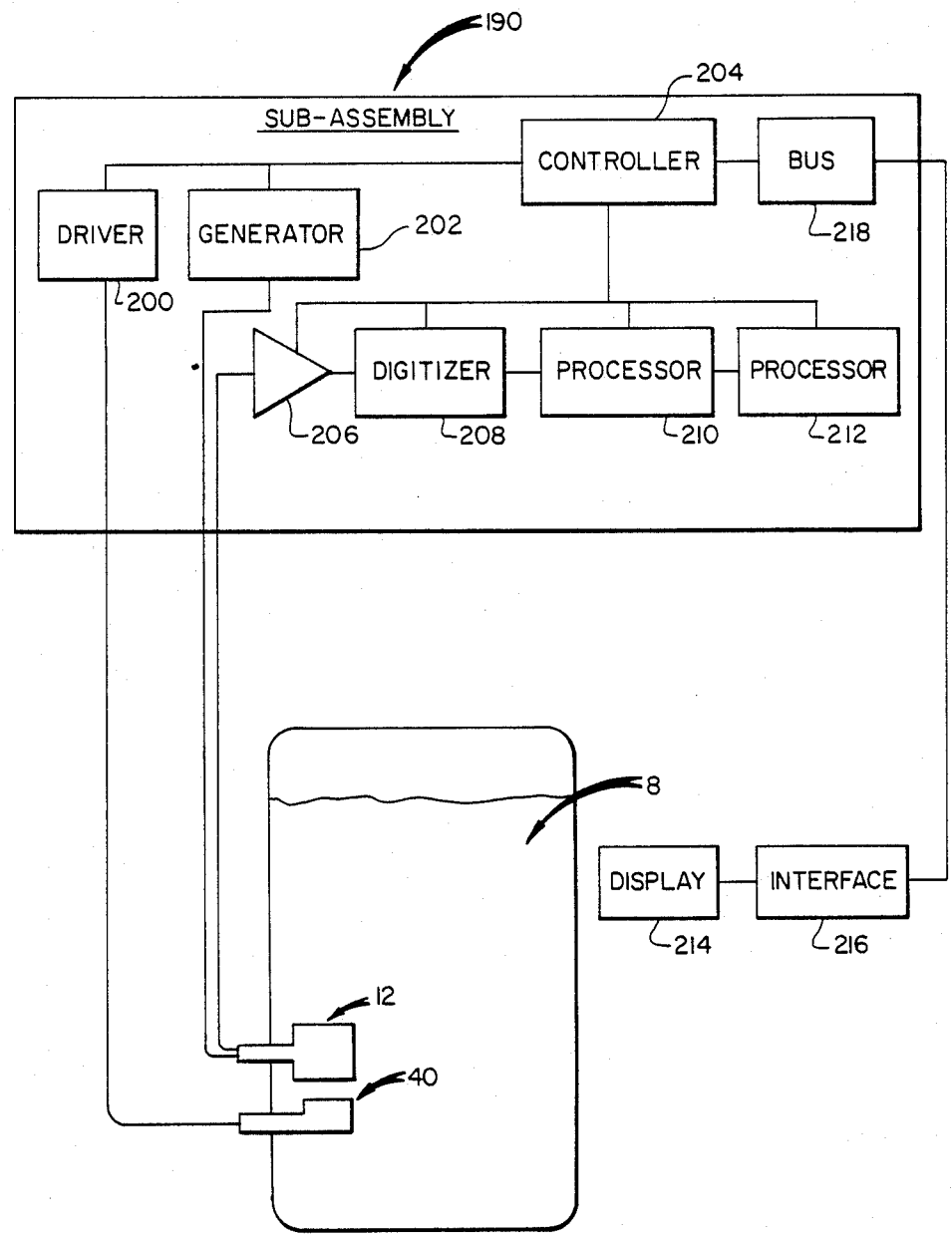
FIG. 3 is a schematic diagram of the power components that operate the apparatus of the invention.

FIG. 3 demonstrates a useful power system for processing such signals. Sub-assembly 190 is a programmable sub-assembly comprising a debubbler driver 200, an ultrasound pulse generating means 202, a microprocessor controller 204, an amplifier 206, a waveform digitizer 208, an FFt processor 210 and a frequency spectra processor 212. The amplifier, digitizer and two processors act to subtract the two echoes received from the transducer. The results are sent to a suitable display 214 via a user interface 216 that connects via a computer bus 218 to the microprocessor 204 and to the pulse generating means. The difference in the two echoes is known to be proportional to the attenuation of the medium. See, e.g., *J. of Acoustical Soc. of America, Vol.* 53, No. 5, Page 1336–42 (1973). The attenuation in turn is proportional to the concentration of cells.

Display 214, interface 216 and computer bus 218 are conventional.

The temporary isolation of the liquid in passageway 18 terminates when gear 28 is reversed to rotate member 12 back to its original position.

It will be readily apparent that, by passageway 18 being free of angles and constrictions, and having projections away from the wall surfaces that do not exceed about 6 mm, that passageway is relatively free of obstructions that can cause build-up of deposits. Furthermore, if deposits do occur, the simplicity of the passageway makes it easy to clean. No tortuous path is present that renders deposits difficult to remove.

Figure 4:
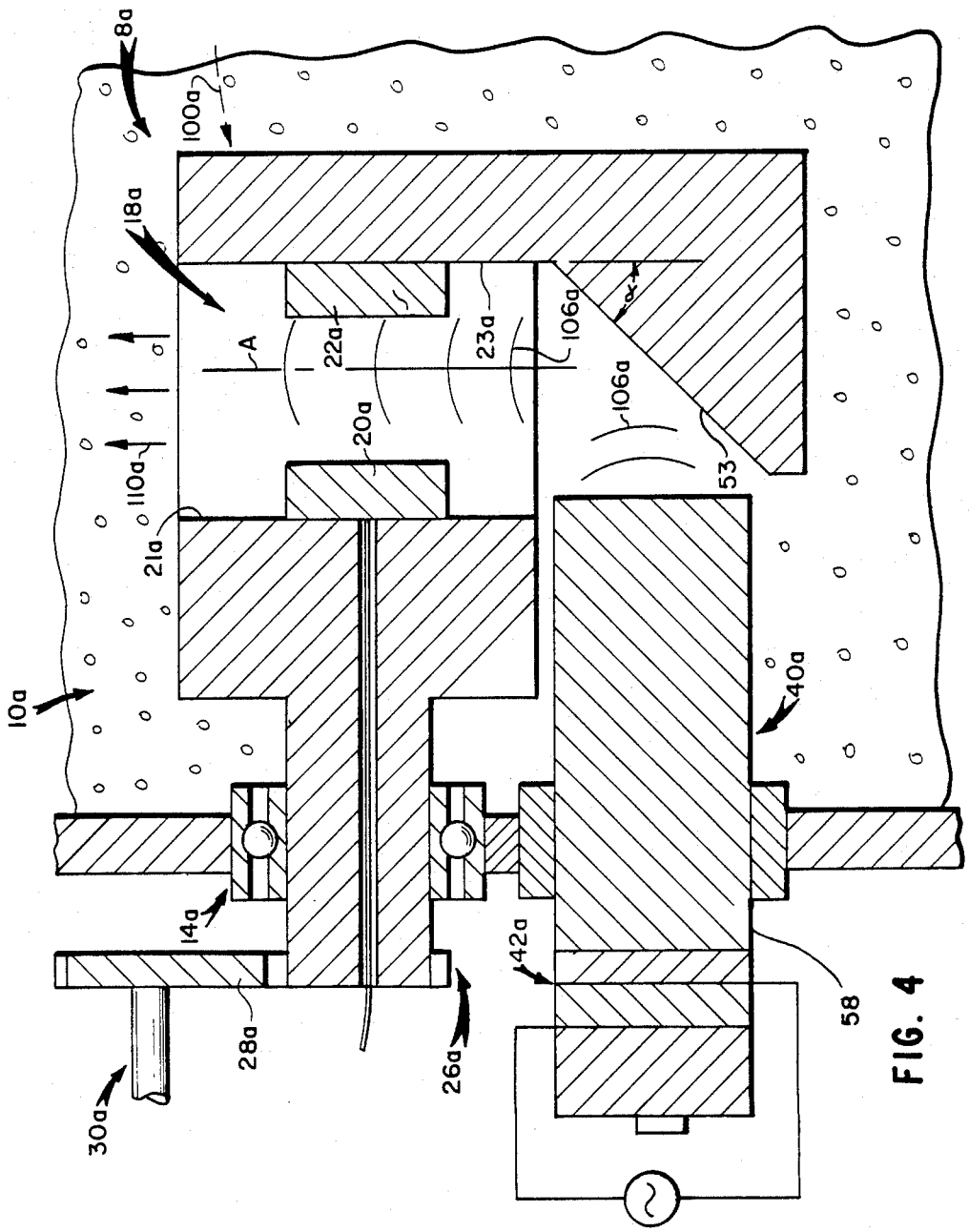
FIG. 4 is an elevational view similar to that of FIG. 1, but illustrating an alternate embodiment.

The flow path of the liquid through passageway 18 will still tolerate some angling, without being totally unsatisfactory from a cleanliness point of view. The alternate embodiment of FIG. 4 illustrates this. Parts similar to those previously described bear the same reference numeral, to which the distinguishing suffix "a" is appended.

Thus, device 10a is mounted in a bearing 14a and has a passageway 18a with a transducer 20a and a target 22a as before. It is rotated by means 26a, 28a and 30a as before. Fixed to the tank below that is debubbler 40a. It comprises a transducer pair 42a connected to an extender or resonator 58. However, in this embodiment, passageway 18a is angled at about 45°, at one end thereof. This is achieved by extending surface 23a at that one end, out and at an angle alpha to the plane of support for target 22a, where alpha is preferably at 45°, to create reflecting surface 53. That suface in turn cooperates with the ultrasonic debubbler horn 40a as follows: Debubbler 40a is aimed generally perpendicularly to the axis A aligned with arrows 110a, and at surface 53, so as to bounce waves 106a off that surface and into passageway 18a. Extender 58 preferably is energized by a piezoelectric sandwich in a conventional manner, and only when passageway 18a has been rotated to isolate it from the current flow of the bath.

When sensing is not being done by transducer 20a, device 10a is rotated 90° so that passageway 18a is lined up with the current flow, arrow 100a (shown here in phantom), in bath 8a. The angle formed by surface 53 is insufficient to interfere with normal current flow through passageway 18a.

Another benefit from the embodiment of FIG. 4 is that the transducer pair 42a is removed to a location external from the bath.

The embodiment of FIG. 4 need not require in all instances, the rotation of passageway 18a to a position 90° out of alignment with current flow path 100a. Instead (not shown), device 10a can be permanently positioned so that flow 100a is permanently aligned with passageway 18a, PROVIDED that flow rate 100a is sufficiently restricted by the position of extender 58 adjacent surface 53 as to cause that flow rate to not exceed the rate at which the debubbler forces bubbles out of passageway 18a. More specifically, it has been found experimentally that using a debubbler horn as taught in U.S. Pat. No. 3,904,392, comprising a solid metal cylinder that is 19 cm long and 3.8 cm in diameter, with target 22a flush with surface 23a, surface 23a being 1.132 cm from surface 21a, transducer 20a projecting from surface 21a a distance of 0.52 cm, and opposite walls 18a being spaced apart with an internal spacing of about 1.91 cm, there is a maximum tolerable flow rate that defines the limits of operability. That is, for such a debubbling horn and a passageway constructed as in the aforesaid U.S. Pat. No. 3,904,392 and similar to that of 18a in FIG. 4, but with the passageway aligned with current flow in the bath, the maximum rates of flow of liquid that can be tolerated before the incoming bubbles overwhelmed the abililty of the horn to force away the bubbles as per arrow 110a, is that set forth in Table I (measured at 40 KHz frequency). (Viscosities were measured at about 40.5 degrees C.)

TABLE I

| Ex. | Bath Viscosity | Horn Power | Velocity | Flow Rate |
|---|---|---|---|---|
| 1 | 20 centipoise | 20 watts | 2.5 cm/sec | 4.3 cc/sec |
| 2 | 20 centipoise | 40 watts | 3.8 cm/sec | 6.5 cc/sec |
| 3 | 60 centipoise | 20 watts | 1.5 cm/sec | 2.6 cc/sec |
| 4 | 60 centipoise | 40 watts | 2.5 cm/sec | 4.3 cc/sec |

It will be readily appreciated that even higher flow rates are useful if the horn power is increased above 40 watts. As a practical matter, however, the flow rate through passageway 18a is preferably much less than these maximum values.

Figures 5, 6:
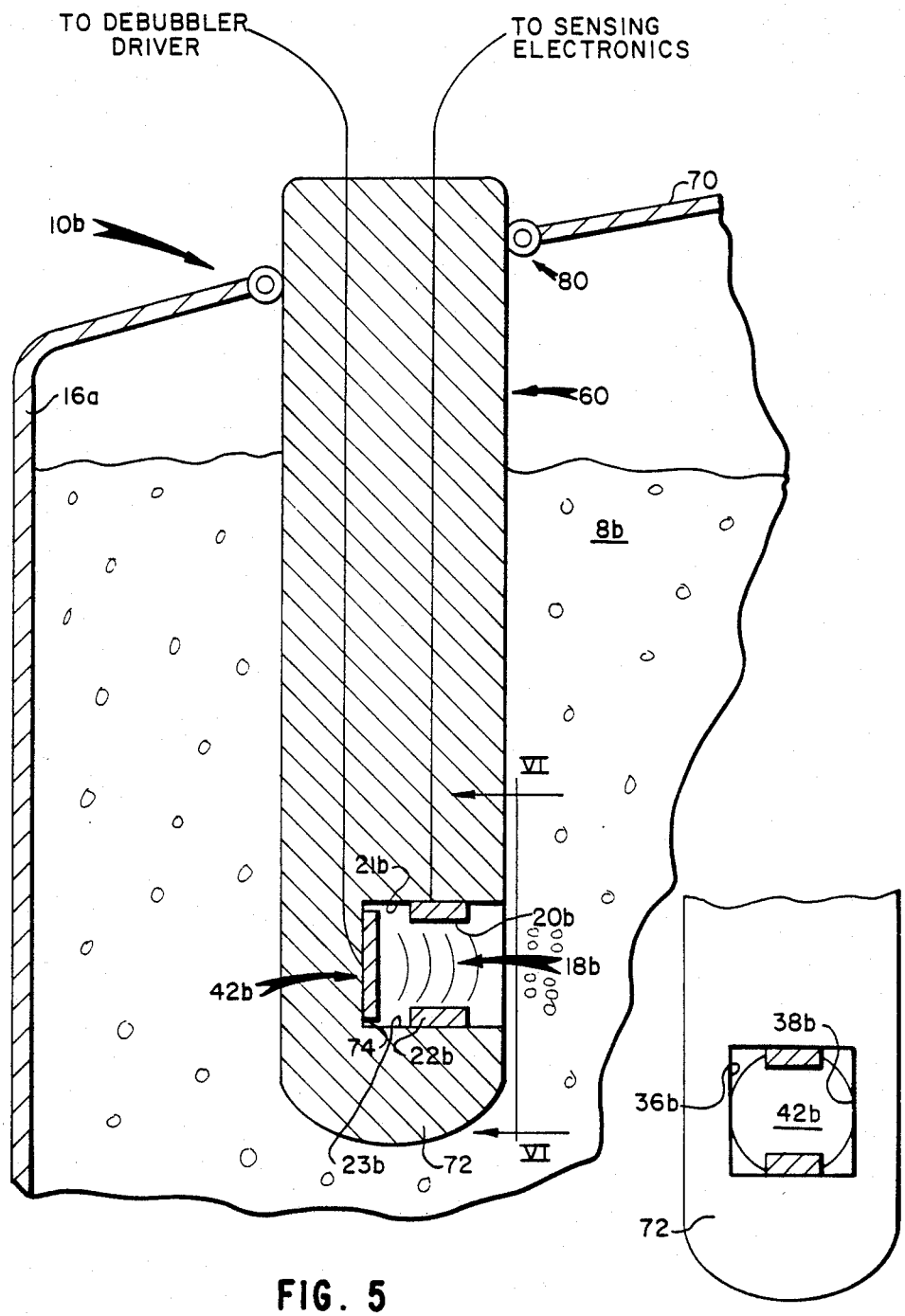
FIG. 5 is a fragmentary elevational view in section of yet another embodiment.
FIG. 6 is a sectional view taken generally along the Line VI—VI of FIG. 5.

In yet another embodiment, there is no, or substantially little, flow of liquid through the sensing device, because the passageway is a dead-end hole that allows for the flow of eddy currents only. One such embodiment is shown in FIGS. 5 and 6. Parts similar to those previously described bear the same reference numeral, to which the distinguishing suffix "b" is applied.

Thus, device 10b comprises a rod mounted, in this case, through the top 70 of tank 16b, so as to extend downwardly into the body of bath 8b. Passageway 18b is a hole in end 72 of the rod, having a bottom surface 74 and two side surfaces 21b and 23b. The other side surfaces 36b and 38b are constructed as before, FIG. 6. Mounted on the side surfaces 21b and 23b are the transducer 20b and the target 22b, as in the previous embodiments. Mounted on surface 74 is the debubbler ultrasonic transducer 42b. Unlike the previous embodiment, surface 74 closes off the passageway so that only eddy currents and not a complete flow-through, occurs in the passageway. Also, surface 74 is fixed to the passageway, so that sensing device 10b need not be rotated from an open position to a "closed" position, as in the other two embodiments. Instead, device 10b is fixed at 80 to wall 16b. The low rate of eddy flow into the dead-end passageway ensures that the debubbling waves 106b will drive out bubbles, FIG. 5, long enough to allow transducer 20b and target 22b to make the sensing measurement.

Figure 7A:
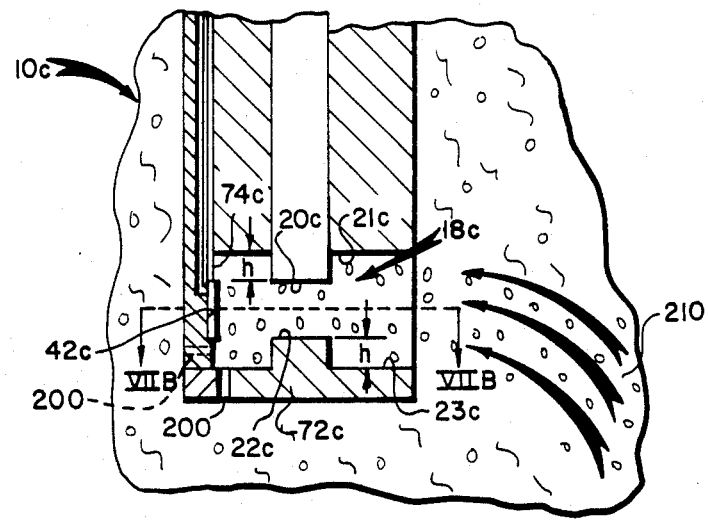
FIG. 7A and 7C are elevational views similar to that of FIG. 5, but of still another embodiment.
Figure 7C:
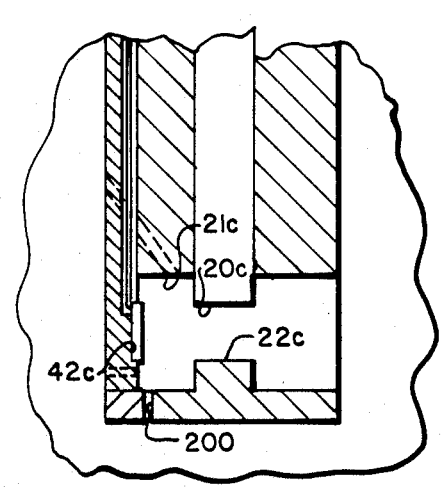
Figure 7B:
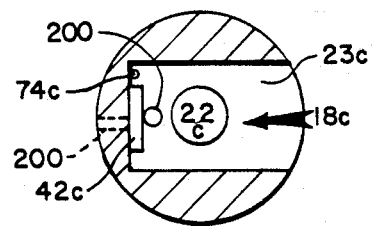
FIG. 7B is a sectional view taken along the line VIIB—VIIB of FIG. 7A.

In yet another embodiment, FIGS. 7A-7C, the passageway past the ultrasound transducer and target is neither completely open, as in the first embodiment, nor completely closed off at one end, as in the last-described embodiment. Instead, a reduced rate of flow through the passageway is provided. Parts similar to those previously described bear the same reference numeral, to which the distinguishing suffix "c" is appended.

Thus, device 10c features, FIG. 7A, a rod fixedly depending downwardly into a tank as described for FIG. 5, with a passageway 18c formed at end 72c of the rod. Side surfaces 21c and 23c have mounted thereon, transducer 20c and target 22c, each protruding no more than distance "h" as in all the other embodiments. Debubbler transducer 42c is mounted on bottom surface 74pc as before. However, unlike the previous embodiment, the wall surfaces do not completely close off passageway 18c from all flow there through. Instead, a bleed aperture 201 is formed, either in side surface 23c as shown, in bottom surface 74c as shown in phantom, or in surface 21c also shown in phantom. The bleed aperture out from surface 21c also aids in removing any large air bubbles trapped on assembly. aperture 201 is no larger in flow-through diameter than that which will allow bubble-containing liquid to flow completely through passageway 18c at a rate that does exceed the ability of transducer 42c to force the bubbles out. The criticality of this flow rate is as follows: FIG. 7c, when transducer 42c is activated, the bubbles are blown out of passageway 18c, leaving the space between transducer 20c and target 22c clear of bubbles so that the ultrasonic sensing measurement can be made. If aperture 201 were so large as to permit the flow to exceed the above-noted flow rate, bubble-containing liquid would flow back in via arrows 210, FIG. 7A, at a rate that exceeds the ability of transducer 42c to force the bubbles out.

The ability to remove the bubbles is a function of the acoustic power of horn 42c, as well as of the viscosity of the bath, (Surface tension also affects that ability, but to a lesser degree.) The higher the viscosity, the more difficult it is for transducer 42c to "blast away" the bubbles. In addition, as the power of the horn is reduced, so too is its effectiveness. With these parameters in mind, the maximum tolerable flow rate before the debubbler ceases to remove bubbles can be experimentally ascertained in a manner similar to that described above for the embodiment of FIG. 4. As in that embodiment, the most preferred operating conditions are those in which the liquid flow rate is much less than such maximum rates.

The use of some flow rate out through aperture 201 is advantageous since it tends to prevent ultrasonic cavitation from forming tiny bubbles in passageway 18c that can NOT be removed by the debubbling mechanism.

FIG. 8 is indicative of results obtained with the apparatus of the invention, and specifically that of FIG. 7. The bath in this case contained primarily Coryneform at three different concentrations. The response of the system at different frequencies is plotted. The three curves show the increase in attenuation as the concentration increased. Good concentration discrimination is shown from 15 to 45 MHz. These limits can be altered to include additional frequencies by the appropriate selection of conventional ultrasound equipment.

It will be readily appreciated that the aforedescribed apparatus has the following additional advantages:

(a) It is insensitive to the height of the liquid in the bath, as it can be placed at any, and preferably, the lower, levels.

(b) The passageway, by virtue of its smooth surfaces free of significant protrusions and angles, except for those necessarily created by the transducer, is easy to clean and keep clean.

To use this invention with an optical sensor, the following modifications are useful (not shown):

In the embodiment of FIG. 5, the transducer 20b and the target 22b are replaced by a light source and a light detector such as a photocell detector, respectively. Such a light source can be, e.g., a bulb, an LED plus focus lens, or an optical fiber in contact with a focusing lens. As a further alternative, the detector need not be opposite the light source, but can be in position adjacent to the light source, to receive light reflected off surface 23b. In that case surface 23b is part of the sensor.

Yet another alternative is to mount the photocell detector neither directly opposite light source 20b, nor adjacent to it, but rather 90° from it on either wall surface 36b or 38b (FIG. 6), for nephelometric measurements.

Similar modifications will be readily apparent to the embodiments of FIGS. 1–4 and FIGS. 7A–7C, in which a light source and detector are substituted for the transducer and target.

The invention has been described in detail with particular reference to preferred embodiments thereof, but it will be understood that variations and modifications can be effected within the spirit and scope of the invention.

What is claimed is:

1. A combination of an aerated bath in which gas bubbles are constantly being generated, and inside the liquid volume of said bath, apparatus comprising:
   (a) means for sensing mass concentration of a material within the liquid in the bath, including means providing a liquid flow-through volume in said sensing means,
   (b) debubbling means for forcing bubbles from the portion of the liquid in said flow-through volume that is to be sensed by said sensing means, away from said sensing means,
   (c) means for temporarily activating said debubbling means just prior to activating said sensing means, and
   (d) means for limiting liquid flow into said flow-through volume within said sensing means to less than the minimum rate that exceeds the ability of said debubbling means to force away the bubbles from said flow-through volume;

whereby said debubbling means is effective to remove bubbles and said sensing means is effective to sense mass concentration, without removal of liquid from the confines of the bath and before said liquid portion is reaerated.

2. Apparatus as defined in claims 1, wherein said sensing means comprise a light source and a light detector.

3. Apparatus as defined in claim 2, wherein said light detector comprises a photocell detector positioned either opposite to, adjacent to, or at 90° from said light source.

4. For use inside an aerated bath, apparatus comprising:
   (a) means for sensing mass concentration of a material within the liquid in the bath, including means providing a liquid flow-through volume in said sensing means, said sensing means comprising an ultrasound transducer, a target spaced away from said transducer and said target, whereby liquid can flow past said sensing means,
   (b) ultrasonic debubbling means comprising an ultrasonic transducer having a frequency different from that of said sensing means, and means for driving said transducer at a frequency of between about 20 KHz and about 5 MHz, and
   (c) means for limiting liquid flow into said flow-through volume within said sensing means to less than the minimum rate that exceeds the ability of said debubbling means to force away the bubbles from said flow-through volume;

whereby the debubbling means is effective to remove bubbles and the sensing means is effective to sense mass concentration, without removal of liquid from the confines of the bath and before said liquid portion is reaerated.

5. Apparatus as defined in claim 4, wherein said flow-limiting means limits the liquid flow rate to no more than about 6.5 cc/sec for debubbling means operated at 40 watts and 40 KHz, in a bath of liquid having a viscosity of 20 centipoise.

6. Apparatus as defined in claim 4 wherein said use is with a fermentation bath and further including means mountable outside of said fermentation bath for porcessing an ultrasound signal received by said sensor into an indication of protein or cell concentration.

7. Apparatus as defined in claim 4, wherein said passageway is free of protrusions projecting into the liquid path from the side walls thereof with a height greater than about 6 mm.

8. Apparatus as defined in claim 1 or 4, and further including means for movably mounting said sensing means to move between a first position in which said passageway is aligned with the direction of liquid flow within said bath, and a second position in which said passageway is misaligned,
and wherein said passageway extends all the way through said sensing means to permit flow of liquid as determined by liquid flow in the bath.

9. Apparatus as defined in claim 8, wherein said mounting means includes a bearing that permits rotation of said sensing means.

10. A process for sensing the mass concentration of an aerated liquid, comprising the steps of
(a) positioning within a mass of liquid in which gas bubbles are constantly being generated, and adjacent to a predetermined flow-through volume of the liquid, (i) sensing means for sensing the mass concentration, and (ii) adjacent to said sensing means, debubbling means for forcing bubbles away from said sensing means,
(b) activating said debubbling means to force bubbles in the vicinity of the sensing means away from the sensing means,
(c) while activating said debubbling means, limiting liquid flow into said flow-through volume, to less than the minimum rate that exceeds the ability of said debubbling means to force away the bubbles from said flow-through volume, and
(d) also while activating said debubbling means for a given volume of said liquid, sensing the mass concentration of that volume of liquid using said sensing means.

* * * * *

UNITED STATES PATENT AND TRADEMARK OFFICE
CERTIFICATE OF CORRECTION

PATENT NO. : 4,825,688

DATED : May 2, 1989

INVENTOR(S) : Robert J. Kraus, Jr.; Peter E. Davison

It is certified that error appears in the above-identified patent and that said Letters Patent is hereby corrected as shown below:

Column 1, Title page, underneath item [76] insert
--Assignee: Eastman Kodak Company,
Rochester, N.Y.--.

Column 2, Title page, underneath Primary Examiner insert
--Attorney, Agent, of Firm - Dana M. Schmidt--.

Signed and Sealed this

Seventeenth Day of April, 1990

Attest:

HARRY F. MANBECK, JR.

Attesting Officer

Commissioner of Patents and Trademarks